United States Patent
Nadjafizadeh et al.

(10) Patent No.: US 9,084,865 B2
(45) Date of Patent: Jul. 21, 2015

(54) SYSTEM AND METHOD FOR REGULATING A HEATING HUMIDIFIER

(75) Inventors: Hossein Nadjafizadeh, Villers lès Nancy (FR); Yves Gaudard, Malzeville (FR); Benjamin Desfossez, Vandoeuvre-lès-Nancy (FR); Patrick Michel, Nancy (FR)

(73) Assignee: COVIDIEN AG, Neuhausen (CH)

( * ) Notice: Subject to any disclaimer, the term of this patent is extended or adjusted under 35 U.S.C. 154(b) by 1549 days.

(21) Appl. No.: 11/686,880

(22) Filed: Mar. 15, 2007

(65) Prior Publication Data
US 2007/0284361 A1   Dec. 13, 2007

Related U.S. Application Data

(63) Continuation of application No. PCT/EP2005/009950, filed on Sep. 15, 2005.

(30) Foreign Application Priority Data

Sep. 15, 2004 (FR) ....................................  04 52060

(51) Int. Cl.
  *F27D 11/00*  (2006.01)
  *H05B 3/02*  (2006.01)
  (Continued)

(52) U.S. Cl.
  CPC .............. *A61M 16/16* (2013.01); *A61M 16/109* (2014.02); *A47J 27/004* (2013.01); *A61M 16/0683* (2013.01); *H01L 21/67248* (2013.01)

(58) Field of Classification Search
  CPC ............ A47J 27/004; H01L 21/67248; G05D 23/1951; G05D 23/2401; H05B 1/0213; A61M 16/16

USPC ................. 219/442, 482, 492, 497, 499, 508; 128/203.17
See application file for complete search history.

(56) References Cited

U.S. PATENT DOCUMENTS 3,903,883 A * 9/1975 Pecina et al. ............. 128/200.21
3,987,133 A   10/1976 Andra
(Continued)

FOREIGN PATENT DOCUMENTS

EP     1197237 A2    4/2002    ............ A61M 16/16
GB     1294808       11/1972   ............ A61M 16/00
(Continued)

OTHER PUBLICATIONS

International Search Report with Written Opinion PCT/EP2005/009950, 9 pages, Nov. 18, 2005.
(Continued)

*Primary Examiner* — Dana Ross
*Assistant Examiner* — Hemant Mathew

(57) ABSTRACT

A method for supplying a mask through which air flows with a regulated degree of humidification (m) is provided. The method may include: providing a water reservoir configured such that the air circulates in contact with the surface of water within the reservoir is charged with humidity; providing a heating device for heating the water in the reservoir by circulating an electric current; measuring an average intensity ($I_{av}$) of the current passing through the heating device; and controlling the average intensity ($I_{av}$) relative to a reference value ($I_{av_c}$) to obtain a degree of humidification (m) of the air that is independent of the ambient temperature (Ta). An apparatus for regulating the degree of humidification of air flow, as well as a heating humidifier including such a regulation device, are also provided.

9 Claims, 3 Drawing Sheets

(51) Int. Cl.

| | |
|---|---|
| *B23K 13/08* | (2006.01) |
| *B23K 15/02* | (2006.01) |
| *A61M 16/16* | (2006.01) |
| *A61M 16/10* | (2006.01) |
| *A47J 27/00* | (2006.01) |
| *H01L 21/67* | (2006.01) |
| *A61M 16/06* | (2006.01) |

(56) References Cited

U.S. PATENT DOCUMENTS

| | | | |
|---|---|---|---|
| 4,146,775 A * | 3/1979 | Kirchner et al. | 392/327 |
| 4,572,427 A | 2/1986 | Selfridge et al. | |
| 4,585,926 A * | 4/1986 | Easthill | 219/506 |
| 4,701,415 A | 10/1987 | Dutton et al. | |
| 4,752,089 A | 6/1988 | Carter | |
| 4,913,140 A | 4/1990 | Orec et al. | |
| 4,921,642 A | 5/1990 | LaTorraca | |
| 4,953,546 A * | 9/1990 | Blackmer et al. | 128/203.16 |
| 4,954,799 A | 9/1990 | Kumar | |
| 5,057,822 A | 10/1991 | Hoffman | |
| 5,062,145 A | 10/1991 | Zwaan et al. | |
| 5,072,737 A | 12/1991 | Goulding | |
| 5,119,807 A | 6/1992 | Roberts et al. | |
| 5,140,255 A * | 8/1992 | Tardio et al. | 323/322 |
| 5,150,291 A | 9/1992 | Cummings et al. | |
| 5,161,525 A | 11/1992 | Kimm et al. | |
| 5,178,138 A | 1/1993 | Walstrom et al. | |
| 5,237,987 A | 8/1993 | Anderson et al. | |
| 5,271,389 A | 12/1993 | Isaza et al. | |
| 5,279,549 A | 1/1994 | Ranford | |
| 5,299,568 A | 4/1994 | Forare et al. | |
| 5,301,921 A | 4/1994 | Kumar | |
| 5,319,540 A | 6/1994 | Isaza et al. | |
| 5,322,057 A | 6/1994 | Raabe et al. | |
| 5,325,861 A | 7/1994 | Goulding | |
| 5,333,606 A | 8/1994 | Schneider et al. | |
| 5,339,807 A | 8/1994 | Carter | |
| 5,343,857 A | 9/1994 | Schneider et al. | |
| 5,351,522 A | 10/1994 | Lura | |
| 5,354,965 A * | 10/1994 | Lee | 219/202 |
| 5,357,946 A | 10/1994 | Kee et al. | |
| 5,367,604 A | 11/1994 | Murray | |
| 5,368,019 A | 11/1994 | LaTorraca | |
| 5,383,449 A | 1/1995 | Forare et al. | |
| 5,385,142 A | 1/1995 | Brady et al. | |
| 5,388,571 A | 2/1995 | Roberts et al. | |
| 5,390,666 A | 2/1995 | Kimm et al. | |
| 5,396,883 A | 3/1995 | Knupp et al. | |
| 5,401,135 A | 3/1995 | Stoen et al. | |
| 5,402,796 A | 4/1995 | Packer et al. | |
| 5,407,174 A | 4/1995 | Kumar | |
| 5,413,110 A | 5/1995 | Cummings et al. | |
| 5,438,980 A | 8/1995 | Phillips | |
| 5,443,075 A | 8/1995 | Holscher | |
| 5,445,143 A | 8/1995 | Sims | |
| 5,452,714 A | 9/1995 | Anderson et al. | |
| 5,513,631 A | 5/1996 | McWilliams | |
| 5,517,983 A | 5/1996 | Deighan et al. | |
| 5,520,071 A | 5/1996 | Jones | |
| 5,524,615 A | 6/1996 | Power | |
| 5,531,221 A | 7/1996 | Power | |
| 5,537,996 A | 7/1996 | McPhee | |
| 5,537,997 A | 7/1996 | Mechlenburg et al. | |
| 5,539,854 A | 7/1996 | Jones et al. | |
| 5,542,415 A | 8/1996 | Brody | |
| 5,544,674 A | 8/1996 | Kelly | |
| 5,549,106 A | 8/1996 | Gruenke et al. | |
| 5,570,684 A * | 11/1996 | Behr | 128/201.13 |
| 5,578,753 A * | 11/1996 | Weiss et al. | 73/335.02 |
| 5,584,285 A | 12/1996 | Salter et al. | |
| 5,588,423 A | 12/1996 | Smith | |
| 5,596,984 A | 1/1997 | O'Mahony et al. | |
| 5,616,115 A | 4/1997 | Gloyd et al. | |
| 5,630,411 A | 5/1997 | Holscher | |
| 5,632,270 A | 5/1997 | O'Mahony et al. | |
| 5,640,951 A | 6/1997 | Huddart et al. | |
| 5,645,048 A | 7/1997 | Brodsky et al. | |
| 5,655,522 A | 8/1997 | Mechlenburg et al. | |
| 5,660,171 A | 8/1997 | Kimm et al. | |
| 5,664,560 A | 9/1997 | Merrick et al. | |
| 5,664,562 A | 9/1997 | Bourdon | |
| 5,666,946 A | 9/1997 | Langenback | |
| 5,671,767 A | 9/1997 | Kelly | |
| 5,672,041 A | 9/1997 | Ringdahl et al. | |
| 5,673,687 A | 10/1997 | Dobson et al. | |
| 5,673,689 A | 10/1997 | Power | |
| 5,713,349 A | 2/1998 | Keaney et al. | |
| 5,715,812 A | 2/1998 | Deighan et al. | |
| 5,758,018 A * | 5/1998 | Fowler, Jr. | 392/402 |
| 5,762,480 A | 6/1998 | Adahan | |
| 5,769,071 A * | 6/1998 | Turnbull | 128/203.12 |
| 5,771,884 A | 6/1998 | Yarnall et al. | |
| 5,791,339 A | 8/1998 | Winter | |
| 5,794,986 A | 8/1998 | Gansel et al. | |
| 5,813,399 A | 9/1998 | Isaza et al. | |
| 5,823,179 A | 10/1998 | Grychowski et al. | |
| 5,826,575 A | 10/1998 | Lall | |
| 5,829,441 A | 11/1998 | Kidd et al. | |
| 5,857,062 A | 1/1999 | Bergamaschi et al. | |
| 5,864,938 A | 2/1999 | Gansel et al. | |
| 5,865,168 A | 2/1999 | Isaza | |
| 5,881,717 A | 3/1999 | Isaza | |
| 5,881,723 A | 3/1999 | Wallace et al. | |
| 5,884,623 A | 3/1999 | Winter | |
| 5,909,731 A | 6/1999 | O'Mahony et al. | |
| 5,915,379 A | 6/1999 | Wallace et al. | |
| 5,915,380 A | 6/1999 | Wallace et al. | |
| 5,915,382 A | 6/1999 | Power | |
| 5,918,597 A | 7/1999 | Jones et al. | |
| 5,921,238 A | 7/1999 | Bourdon | |
| 5,934,274 A | 8/1999 | Merrick et al. | |
| 5,988,164 A * | 11/1999 | Paluch | 128/203.26 |
| 6,006,748 A | 12/1999 | Hollis | |
| D418,498 S | 1/2000 | Leonard | |
| 6,019,100 A | 2/2000 | Alving et al. | |
| 6,024,089 A | 2/2000 | Wallace et al. | |
| 6,041,780 A | 3/2000 | Richard et al. | |
| 6,047,860 A | 4/2000 | Sanders | |
| 6,050,260 A | 4/2000 | Daniell et al. | |
| 6,067,984 A | 5/2000 | Piper | |
| 6,076,523 A | 6/2000 | Jones et al. | |
| 6,078,729 A * | 6/2000 | Kopel | 392/402 |
| 6,102,037 A | 8/2000 | Koch | |
| 6,106,479 A | 8/2000 | Wunderlich et al. | |
| 6,116,240 A | 9/2000 | Merrick et al. | |
| 6,116,464 A | 9/2000 | Sanders | |
| 6,123,073 A | 9/2000 | Schlawin et al. | |
| 6,135,106 A | 10/2000 | Dirks et al. | |
| 6,135,432 A | 10/2000 | Hebblewhite et al. | |
| 6,142,150 A | 11/2000 | O'Mahoney | |
| 6,161,539 A | 12/2000 | Winter | |
| 6,204,623 B1 * | 3/2001 | Levy et al. | 318/641 |
| 6,220,245 B1 | 4/2001 | Takabayashi et al. | |
| 6,256,454 B1 | 7/2001 | Dykes | |
| 6,269,810 B1 | 8/2001 | Brooker et al. | |
| 6,269,812 B1 | 8/2001 | Wallace et al. | |
| 6,273,444 B1 | 8/2001 | Power | |
| 6,283,119 B1 | 9/2001 | Bourdon | |
| 6,305,373 B1 | 10/2001 | Wallace et al. | |
| 6,321,748 B1 | 11/2001 | O'Mahoney | |
| 6,325,785 B1 | 12/2001 | Babkes et al. | |
| 6,338,473 B1 | 1/2002 | Hebblewhite et al. | |
| 6,349,722 B1 | 2/2002 | Gradon et al. | |
| 6,357,438 B1 | 3/2002 | Hansen | |
| 6,360,745 B1 | 3/2002 | Wallace et al. | |
| 6,369,838 B1 | 4/2002 | Wallace et al. | |
| 6,397,841 B1 | 6/2002 | Kenyon et al. | |
| 6,412,483 B1 | 7/2002 | Jones et al. | |
| 6,437,300 B1 * | 8/2002 | Katzman et al. | 219/497 |

(56) References Cited

U.S. PATENT DOCUMENTS

| | | |
|---|---|---|
| 6,439,229 B1 | 8/2002 | Du et al. |
| 6,467,478 B1 | 10/2002 | Merrick et al. |
| 6,510,848 B1 | 1/2003 | Gibertoni |
| 6,543,701 B1 | 4/2003 | Ho |
| 6,546,930 B1 | 4/2003 | Emerson et al. |
| 6,553,991 B1 | 4/2003 | Isaza |
| 6,554,260 B1 | 4/2003 | Lipscombe et al. |
| 6,557,549 B2 | 5/2003 | Schmidt et al. |
| 6,557,553 B1 | 5/2003 | Borrello |
| 6,557,555 B1 | 5/2003 | Hollis |
| 6,571,795 B2 | 6/2003 | Bourdon |
| 6,576,358 B2 | 6/2003 | Gebhardt et al. |
| 6,581,600 B2 | 6/2003 | Bird |
| 6,584,972 B2 * | 7/2003 | McPhee ............ 128/203.17 |
| 6,591,834 B1 | 7/2003 | Colla et al. |
| 6,615,824 B2 | 9/2003 | Power |
| 6,622,726 B1 | 9/2003 | Du |
| 6,644,310 B1 | 11/2003 | Delache et al. |
| 6,668,824 B1 | 12/2003 | Isaza et al. |
| 6,675,801 B2 | 1/2004 | Wallace et al. |
| 6,694,974 B1 | 2/2004 | Gradon et al. |
| 6,705,316 B2 | 3/2004 | Blythe et al. |
| 6,718,974 B1 | 4/2004 | Moberg |
| 6,725,447 B1 | 4/2004 | Gilman et al. |
| 6,739,337 B2 | 5/2004 | Isaza |
| D492,399 S | 6/2004 | Jenkinson |
| 6,745,768 B2 | 6/2004 | Colla et al. |
| 6,761,167 B1 | 7/2004 | Nadjafizadeh et al. |
| 6,761,168 B1 | 7/2004 | Nadjafizadeh et al. |
| 6,782,888 B1 | 8/2004 | Friberg et al. |
| 6,802,314 B2 * | 10/2004 | McPhee ............ 128/203.17 |
| 6,805,118 B2 | 10/2004 | Brooker et al. |
| 6,807,965 B1 | 10/2004 | Hickle |
| D498,527 S | 11/2004 | Virr et al. |
| 6,814,074 B1 | 11/2004 | Nadjafizadeh et al. |
| 6,866,040 B1 | 3/2005 | Bourdon |
| 6,904,911 B2 | 6/2005 | Gibertoni |
| 6,935,337 B2 | 8/2005 | Virr et al. |
| 6,948,491 B2 | 9/2005 | Loeffler et al. |
| 6,960,854 B2 | 11/2005 | Nadjafizadeh et al. |
| 6,968,840 B2 | 11/2005 | Smith et al. |
| 6,968,841 B2 | 11/2005 | Fini |
| 7,032,590 B2 | 4/2006 | Loeffler et al. |
| 7,036,504 B2 | 5/2006 | Wallace et al. |
| 7,040,317 B2 | 5/2006 | Colla et al. |
| 7,051,733 B2 * | 5/2006 | Gradon et al. ...... 128/203.17 |
| 7,059,325 B2 | 6/2006 | Hollis |
| 7,077,131 B2 | 7/2006 | Hansen |
| RE39,225 E | 8/2006 | Isaza et al. |
| 7,096,864 B1 | 8/2006 | Mayer et al. |
| 7,100,600 B2 | 9/2006 | Loeffler et al. |
| 7,106,955 B2 | 9/2006 | Thudor et al. |
| 7,117,438 B2 | 10/2006 | Wallace et al. |
| 7,137,388 B2 | 11/2006 | Virr et al. |
| 7,146,979 B2 | 12/2006 | Seakins et al. |
| 7,191,780 B2 | 3/2007 | Faram |
| 7,195,011 B2 | 3/2007 | Loeffler et al. |
| 7,201,167 B2 | 4/2007 | Fink et al. |
| 7,201,734 B2 | 4/2007 | Hickle |
| D542,900 S | 5/2007 | Snow et al. |
| 7,219,666 B2 | 5/2007 | Friberg et al. |
| RE39,724 E | 7/2007 | Gradon et al. |
| 7,241,269 B2 | 7/2007 | McCawley et al. |
| D549,321 S | 8/2007 | Snow et al. |
| D549,810 S | 8/2007 | Smith et al. |
| 7,263,994 B2 | 9/2007 | Gradon et al. |
| 7,267,121 B2 | 9/2007 | Ivri |
| 7,270,126 B2 | 9/2007 | Wallace et al. |
| D555,236 S | 11/2007 | Snow et al. |
| 7,290,541 B2 | 11/2007 | Ivri et al. |
| D557,407 S | 12/2007 | Lithgow et al. |
| 7,306,205 B2 | 12/2007 | Huddart et al. |
| 7,308,894 B2 | 12/2007 | Hickle |
| D559,371 S | 1/2008 | Snow et al. |
| D559,964 S | 1/2008 | Snow et al. |
| 7,322,349 B2 | 1/2008 | Power |
| D561,890 S | 2/2008 | Lithgow et al. |
| D561,891 S | 2/2008 | Lithgow et al. |
| 7,331,339 B2 | 2/2008 | Smith et al. |
| 7,335,157 B2 | 2/2008 | Czupich et al. |
| D569,958 S | 5/2008 | Snow et al. |
| 7,369,757 B2 | 5/2008 | Farbarik |
| 7,370,650 B2 | 5/2008 | Nadjafizadeh et al. |
| 7,413,173 B2 | 8/2008 | DiMatteo et al. |
| D576,263 S | 9/2008 | Snow et al. |
| 7,428,902 B2 | 9/2008 | Du et al. |
| D579,537 S | 10/2008 | Smith et al. |
| 7,460,959 B2 | 12/2008 | Jafari |
| 7,487,773 B2 | 2/2009 | Li |
| 7,549,421 B2 | 6/2009 | Levi et al. |
| 7,565,905 B2 | 7/2009 | Hickle |
| 7,600,511 B2 | 10/2009 | Power et al. |
| 7,607,431 B1 | 10/2009 | Cruitt et al. |
| 7,607,436 B2 | 10/2009 | Smaldone et al. |
| 7,654,802 B2 | 2/2010 | Crawford, Jr. et al. |
| 7,686,014 B2 | 3/2010 | Boehm et al. |
| 7,694,677 B2 | 4/2010 | Tang |
| 7,748,377 B2 | 7/2010 | Smith et al. |
| 7,784,461 B2 | 8/2010 | Figueiredo et al. |
| 7,802,569 B2 | 9/2010 | Yeates et al. |
| 7,823,588 B2 | 11/2010 | Hansen |
| 7,849,853 B2 | 12/2010 | Grychowski et al. |
| 7,855,716 B2 | 12/2010 | McCreary et al. |
| 7,891,354 B2 | 2/2011 | Farbarik |
| 7,984,714 B2 | 7/2011 | Hausmann et al. |
| 8,021,310 B2 | 9/2011 | Sanborn et al. |
| 8,210,173 B2 | 7/2012 | Vandine |
| 8,210,174 B2 | 7/2012 | Farbarik |
| 2002/0017298 A1 | 2/2002 | Koch |
| 2002/0063122 A1 * | 5/2002 | Katzman et al. ............ 219/497 |
| 2002/0083947 A1 | 7/2002 | Seakins |
| 2002/0129815 A1 | 9/2002 | McPhee |
| 2002/0139367 A1 * | 10/2002 | McPhee ............ 128/203.17 |
| 2003/0079748 A1 | 5/2003 | Seakins |
| 2004/0035413 A1 | 2/2004 | Smaldone et al. |
| 2004/0074493 A1 | 4/2004 | Seakins et al. |
| 2004/0079370 A1 | 4/2004 | Gradon et al. |
| 2004/0182386 A1 | 9/2004 | Meier |
| 2004/0226561 A1 | 11/2004 | Colla et al. |
| 2004/0229089 A1 | 11/2004 | Preidel et al. |
| 2005/0039748 A1 | 2/2005 | Andrieux |
| 2005/0139212 A1 | 6/2005 | Bourdon |
| 2005/0178383 A1 * | 8/2005 | Mackie et al. .......... 128/203.16 |
| 2005/0217666 A1 | 10/2005 | Fink et al. |
| 2005/0229927 A1 | 10/2005 | Fink et al. |
| 2005/0284469 A1 | 12/2005 | Tobia et al. |
| 2006/0037613 A1 | 2/2006 | Kwok et al. |
| 2006/0130836 A1 | 6/2006 | Wixey et al. |
| 2006/0137687 A1 | 6/2006 | Colla et al. |
| 2006/0144395 A1 | 7/2006 | Koch et al. |
| 2006/0231097 A1 | 10/2006 | Dougherty et al. |
| 2006/0237005 A1 | 10/2006 | Virr et al. |
| 2007/0017515 A1 | 1/2007 | Wallace et al. |
| 2007/0077200 A1 | 4/2007 | Baker |
| 2007/0083677 A1 | 4/2007 | Cecka et al. |
| 2007/0132117 A1 | 6/2007 | Pujol et al. |
| 2007/0157928 A1 | 7/2007 | Pujol et al. |
| 2007/0157931 A1 | 7/2007 | Parker et al. |
| 2007/0213658 A1 | 9/2007 | Hickle |
| 2007/0227537 A1 | 10/2007 | Bemister et al. |
| 2007/0267010 A1 | 11/2007 | Fink et al. |
| 2008/0017198 A1 | 1/2008 | Ivri |
| 2008/0021379 A1 | 1/2008 | Hickle |
| 2008/0053441 A1 | 3/2008 | Gottlib et al. |
| 2008/0072896 A1 | 3/2008 | Setzer et al. |
| 2008/0072900 A1 | 3/2008 | Kenyon et al. |
| 2008/0072902 A1 | 3/2008 | Setzer et al. |
| 2008/0072904 A1 | 3/2008 | Becker et al. |
| 2008/0078390 A1 | 4/2008 | Milne et al. |

(56) References Cited

U.S. PATENT DOCUMENTS

| | | |
|---|---|---|
| 2008/0083644 A1 | 4/2008 | Janbakhsh et al. |
| 2008/0142002 A1 | 6/2008 | Fink et al. |
| 2008/0149096 A1 | 6/2008 | Power |
| 2008/0216829 A1 | 9/2008 | Koch et al. |
| 2008/0295830 A1 | 12/2008 | Martonen et al. |
| 2008/0302361 A1 | 12/2008 | Snow et al. |
| 2008/0302362 A1 | 12/2008 | Kwok |
| 2009/0000620 A1 | 1/2009 | Virr |
| 2009/0205655 A1 | 8/2009 | Montgomery et al. |

FOREIGN PATENT DOCUMENTS

| | | | |
|---|---|---|---|
| JP | 11057009 A | 3/1999 | ............ A61M 16/00 |
| WO | 2004020031 A1 | 3/2004 | ............ A61M 16/16 |

OTHER PUBLICATIONS

Japanese Office Action with English translation, JP Application No. 2007-531685, 10 pages, Jan. 11, 2011.

7200 Series Ventilator, Options, and Accessories: Operators Manual. Nellcor Puritan Bennett, Part No. 22300 A, Sep. 1990, pp. 1-196.

7200 Ventilatory System: Addendum/Errata. Nellcor Puritan Bennett, Part No. 4-023576-00, Rev. A, Apr. 1998, pp. 1-32.

800 Operator's and Technical Reference Manual. Series Ventilator System, Nellcor Puritan Bennett, Part No. 4-070088-00, Rev. L, Aug. 2010, pp. 1-476.

840 Operator's and Technical Reference Manual. Ventilator System, Nellcor Puritan Bennett, Part No. 4-075609-00, Rev. G, Oct. 2006, pp. 1-424.

* cited by examiner

> US 9,084,865 B2

SYSTEM AND METHOD FOR REGULATING A HEATING HUMIDIFIER

CROSS-REFERENCE TO RELATED APPLICATION

This application is a continuation of co-pending International Application No. PCT/EP2005/009950 filed Sep. 15, 2005, which designates the United States, and claims priority to French application number 0452060 filed Sep. 15, 2004.

TECHNICAL FIELD

The invention concerns a process for supplying a mask with air with a regulated degree of humidification, a regulation device for the degree of humidification of an air flow, as well as a heating humidifier including such a regulation device.

BACKGROUND

It is known to place a humidifier at the output of a respiratory assistance device that delivers air to a user, so as to humidify the air supplied to the user and thus avoid drying out of the respiratory tract.

In order to obtain sufficient air humidification over the entire range of possible air flow rates (between 0 and 2 L/s), it is prescribed to heat the air contained in a humidifier reservoir, so as to accelerate evaporation and therefore transfer the water molecules to the air delivered to the user.

For the comfort of the user, the humidifier should be able to permit control of the degree of humidification of the supplied air.

Regulation systems of such heating humidifiers are already known that seek to supply the user air having a desired humidity level, for example, an essentially constant humidity level.

A first known system consists of regulating only the water temperature. Hence, the degree of humidification of the air delivered to the user also depends on the temperature of the air, which can vary, especially between day and night. It follows that simple regulation of the water temperature may not permit a constant air humidification level, which may be unsatisfactory.

A second known system employs, on the one hand, a temperature probe for the water, and, on the other hand, a temperature probe for the air. This system has higher performance, because it accounts for ambient conditions. However, such a system requiring the use of two probes may be relatively costly and more complex to use.

SUMMARY

According to some embodiments, a method for supplying a mask through which air flows with a regulated degree of humidification (m) is provided. The method may include: providing a water reservoir configured such that the air circulates in contact with the surface of water within the reservoir is charged with humidity; providing a heating device for heating the water in the reservoir by circulating an electric current; measuring an average intensity (Iav) of the current passing through the heating device; and controlling said average intensity (Iav) relative to a reference value ($Iav_c$) to obtain a degree of humidification (m) of the air that is independent of the ambient temperature (Ta).

In some embodiments, the heating device can be supplied a rectified sinusoidal current including passing half-cycles and blocked half-cycles blocked at 0, and the average intensity of the current passing can be regulated by controlling the number of passing half-cycles during a given time interval.

According to one embodiment, the method may also include:

storing a reference power (Pc) supplied to the heating device, the reference power (Pc) selected by a user;

measuring and storing a peak value (Umax) of a feed voltage for the heating device;

calculating the reference value ($Iav_c$) of the average intensity of the current passing through the heating device based on the reference power (Pc) and the peak value (Umax) of the feed voltage, and storing said reference value ($Iav_c$) of the average intensity;

measuring and storing the average intensity (Iav) of the current passing through the heating device;

comparing the measured value of the average intensity (Iav) and the reference value ($Iav_c$) of the average intensity; and/or controlling the number of passing half-cycles during a given time interval to reduce the difference between the measured value (Iav) of the average intensity and the reference value ($Iav_c$) of the average intensity.

According to other embodiments, an apparatus for regulating the degree of humidification (m) of an air flow circulating in contact with the water surface of water located in a reservoir and intended to be distributed to a user via a mask is provided. The apparatus may include a heating device operable to heat said water by circulating an electric current; means for measuring an average intensity (Iav) of the current passing through the heating device; and means for regulating said average intensity (Iav) relative to a reference value ($Iav_c$).

According to certain embodiments, the apparatus may also include:

selection means allowing a user to select a desired reference power (Pc);

means for measuring a peak value (Umax) of the feed voltage of the heating device and an average intensity (Iav) of the current passing through the heating device;

means for storing the reference power (Pc) and peak value (Umax) of the feed voltage;

means for calculating a reference value ($Iav_c$) of the average intensity of the current passing through the heating device from the reference power (Pc) and the peak value (Umax) of the feed voltage;

means for storing the reference value ($Iav_c$) of the average intensity and the measured average intensity (Iav);

means for comparing the measured value (Iav) and the reference value ($Iav_c$) of the average intensity; and/or means controlled by the comparison device and operable to act on the power supply of the heating device to reduce the difference between the measured value (Iav) and the reference value ($Iav_c$) of the average intensity.

In addition, according to some embodiments, the apparatus may also include a rectification device for rectification of the voltage delivered by the line voltage, and a blocking device operable to block some of the half-cycles of the voltage at 0. The rectification and blocking devices may be configured such that the heating device can be supplied a rectified sinusoidal current including passing half-cycles and half-cycles blocked at 0.

The blocking device may be configured to control the number of half-cycles blocked at 0 during a given time interval as a function of the difference between the measured value (Iav) and the reference value ($Iav_c$) of the average intensity.

According to yet another embodiment, a heating humidifier apparatus includes a water reservoir configured to house water; a heating device operable to heat the water in the reservoir by circulating electric current; an air input and output configured such that an air flow can circulate in contact with the surface of the water and be charged with humidity; and a control device for regulating the degree of humidification of the air flow.

BRIEF DESCRIPTION OF THE DRAWINGS

Other characteristics of various embodiments of the invention are apparent from the following description, a description made with reference to the appended drawings, in which.

DETAILED DESCRIPTION

Figure 1:
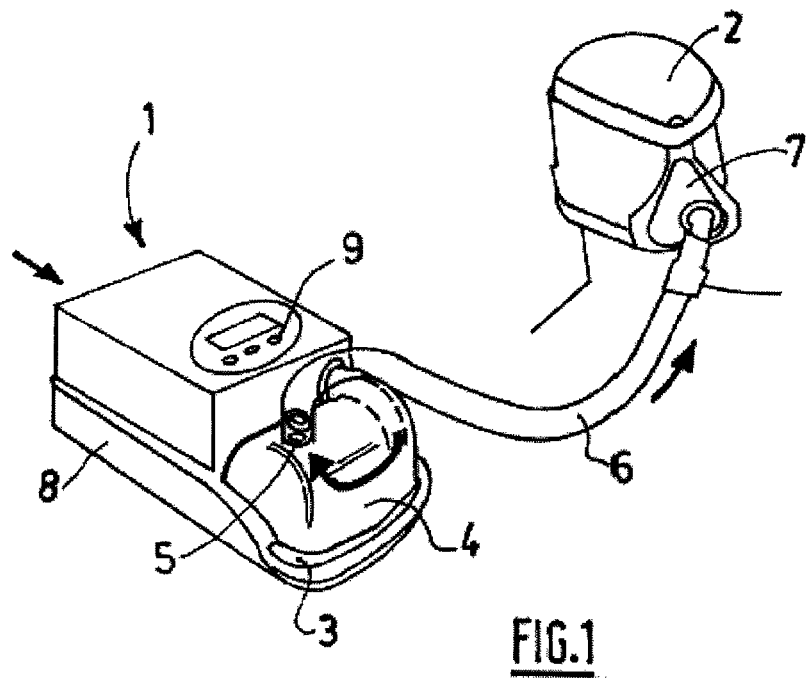
FIG. 1 is a perspective view of a heating humidifier according to one embodiment of the disclosure, including an outlet line associated with a mask applied to the nose and mount of the user.

A heating humidifier 1 is shown in FIG. 1, interposed between a respiratory assistance apparatus and a user 2. For example, the respiratory assistance apparatus may be a medical apparatus for treatment of symptoms of sleep apnea, which may be used in a laboratory or at home.

The heating humidifier 1 may include a heating element, e.g., a metal plate 3 in contact with a resistance.

The resistance may comprise a screen-printed track on an insulated metal support or a resistance on a flexible film glued to a metal support. The heating element may be designed to ensure electrical insulation of 400 Veff between its conducting part (resistance) and its upper face, which may be an accessible part. The trace of this track (coil) may be such that heat transfer is distributed homogenously over the entire metal surface in contact with the water reservoir of heating humidifier 1.

A water reservoir 4 may be positioned on the heated metal plate, a spring system (not shown) keeping the plate in contact with the bottom of reservoir 4 and thus improving heat transfer.

Reservoir 4 may be equipped with an input through which air from the respiratory assistance apparatus enters, and an output connected to a line 6, at the end of which a mask 7 may be connected, which may be intended to be applied to the nose and/or mouth of user 2.

The different elements forming the heating humidifier 1 may be housed in an enclosure made of an insulating material, for example, plastic, and equipped with selection and control devices 9 that can be operated by a user.

The air delivered by the respiratory assistance apparatus may pass through the heating humidifier 1 such that it is charged with humidity on contact with the water surface in reservoir 4. The humidified air leaving the heating humidifier 1 may then be directed to user 2 via line 6 and mask 7 (see the arrows shown in FIG. 1).

In some embodiments, the heating humidifier may be intended to function normally under the following conditions:

| | |
|---|---|
| atmospheric pressure: | 700 hPa to 1060 hPa |
| temperature: | +5° C. to +35° C. |
| relative humidity: | 15% to 95% without condensation |

The use temperature may be limited to 35° C. in order to meet the requirements of the standard, which imposes a maximum air temperature delivered to the user of 41° C.

In order to obtain a desired humidification of the supplied air, the disclosure may provide for controlling the power delivered to the heating element.

It is demonstrated below that regulation of the power may permit a constant humidification level to be obtained, whatever the ambient temperature, without requiring the use of a temperature probe.

If a water surface in contact with an air mass is considered, transfer of water to the air, under the conditions of use of the humidifier, can be described by the equation of Incropera and Dewitt:

$$m=(S/Rw)(h/Cp\, Le^{(1-n)})((Ps_{(Ts)}/Ts)-(Pv_{(Ta)}/Ta)) \quad \text{Equation 1}$$

where:
  m=weight of the water transferred per unit time (in g/s)
  S=water/air exchange surface (in m$^2$)
  Rw=425 J/kg·K (constant related to water)
  h=heat transfer coefficient of water to air (depends on the considered system)
  Cp=1008 J/kg·K (specific heat of water)
  Le=0.846 (Lewis constant)
  n=3 (coefficient, determined empirically in the case of water)
  $Ps_{(Ts)}$=611 exp (17.27×Ts/(237.3+Ts)) (saturation vapor pressure of water at temperature Ts)
  Ts=Surface temperature of the water (in ° C.)
  $Pv_{(Ta)}=Ps_{(Ta)}\times$HR (water vapor pressure at ambient temperature and humidity)
  Ta=Air temperature (in ° C.)
  HR=relative humidity of the air (between 0 and 1)

The factors that intervene in mass transfer and their effect on it are as follows:
  The surface S of air/water exchange:
    All other conditions remaining constant, especially the temperatures of the water and air, Equation 1 is equivalent to: m=cte×S. The degree of humidification is therefore a linear function of the water/air exchange surface.
  The temperature difference between the water and air (Ts−Ta):
    If the water and air are at the same temperature, transfer of water molecules to the air occurs (natural convection), which depends only on the degree of humidity of the air. This transfer is not zero if the relative humidity of air less than 100%.
    If the water is heated so as to increase its temperature a few degrees, greater transfer is produced, the degree of humidification (weight of transfer of water m) being proportional to the temperature difference between the water and air, as shown in FIG. 2.

Figure 2:
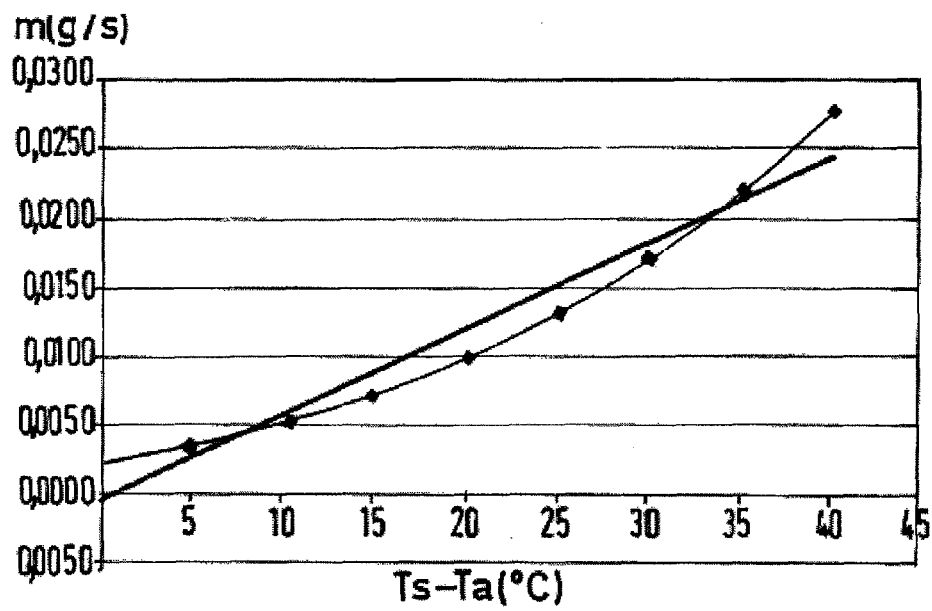
FIG. 2 is a graphic representation showing the calculated water evaporation curve (in g/s) on contact of the air, for an ambient temperature of 25° C., as a function of the temperature difference between the water and the air, as well as the linear approximation of this curve.

The curve in FIG. 2 may be obtained by calculation of Equation 1 using the following values (parameters close to those of one example contemplated application):

| | |
|---|---|
| S = 0.01 m² | h = 20 |
| ρ = 1.2 g/L (volumetric weight of air) | Ta = 25° C. |

It is found, for the user, that the sensation of air humidity can be considered a linear function of the temperature difference between the water and air (linear approximation of the curve of FIG. 2 with a correlation coefficient R=0.952).

Figure 3:
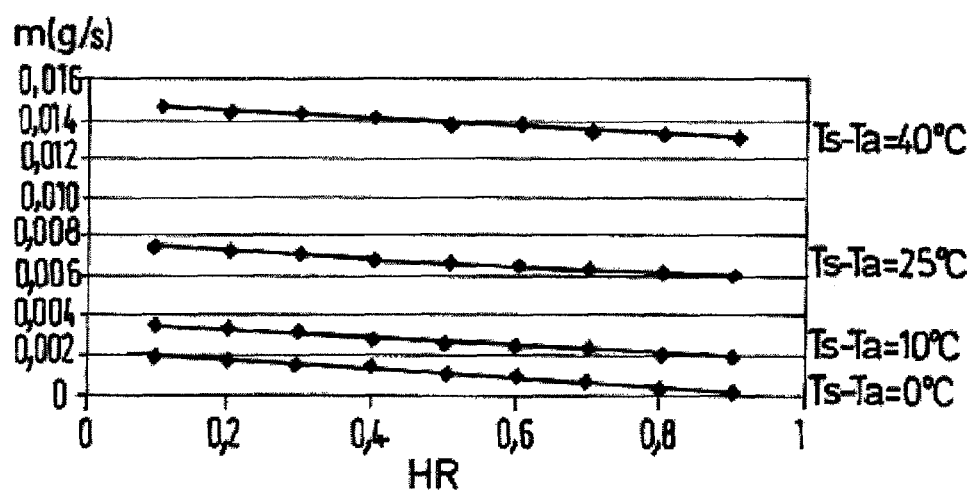
FIG. 3 is a graphic representation showing the calculated evolution of water evaporation (in g/s) on contact of the air, for an ambient temperature of 25° C., as a function of relative humidity of the air for different values of the temperature differences between the water and air.

Humidity of the ambient air (HR):

The curves of FIG. 3 were obtained by calculation of Equation 1 using the following values:

| | |
|---|---|
| S = 0.01 m² | h = 10 |
| Ta = 25° C. | Ts = 25, 35, 50, 65° C. |
| HR varying from 10 to 90% | |

It is found that the degree of humidification m is a linear function of the relative humidity of the ambient air.

The air flow rate (V, in L/s, considered as constant and uniform):

Equation 1 describes exchange of water molecules in static fashion. However, in the humidifier, the reservoir is traversed by air such that during flow, the ambient air replaces the air that was just humidified, thus increasing the degree of humidification relative to the static case.

According to the first law of thermodynamics, we have:

$$P=(Ts-Ta)/Rth \quad \text{Equation 2}$$

where P is the power supplied to the system and Rth is the heat resistance of the system, expressed in K/W.

The heat resistance Rth may depend only on the dimensions of the heat exchange system (its thickness e and the exchange surface S) and the heat transfer coefficients, which depend, for example, on the nature of the materials present. This heat resistance may therefore be a fixed characteristic of the system. Since the heat resistance is inversely proportional to exchange surface, one can write: Rth=cte/S.

For this reason, Equation 2 can be written:

$$P/[(Ts-Ta) \times S]=cte \quad \text{Equation 3}$$

Thus, power regulation permits a constant product (Ts−Ta)×S to be conserved.

This means that for a given exchange surface, the temperature difference between water and air is a linear function of the power supplied to the system. Hence, as mentioned above, the degree of humidification may depend essentially in linear fashion on this temperature difference. All other parameters remaining constant, one can therefore write that: m≈cte×P.

On the other hand, for a constant power, any variation of the exchange surface due, for example, to the variable cross section of the reservoir as a function of the amount of liquid that it contains, may be automatically compensated by an inversely proportional variation of factor (Ts−Ta), which permits the above constant that relates m and P to be left unchanged.

As a result, power regulation may enable us to guarantee a degree of humidification independent of the ambient temperature Ta and the exchange surface of the reservoir.

Nevertheless, this degree of humidification remains dependent on the ambient humidity HR and the flow rate of the air traversing the apparatus (the heat transfer characteristics of the heating element and the reservoir are fixed for a given system).

We will now describe the manner in which the power supply to the system may be controlled, according to this disclosure.

The general principle is to control the power by allowing more or less half-cycles of a rectified sinusoidal signal to pass through, obtained from the line voltage. This has the advantage of permitting adaptation to all possible line voltages by compensating for low voltage with a larger number of passing half-cycles and vice versa.

Figure 4:
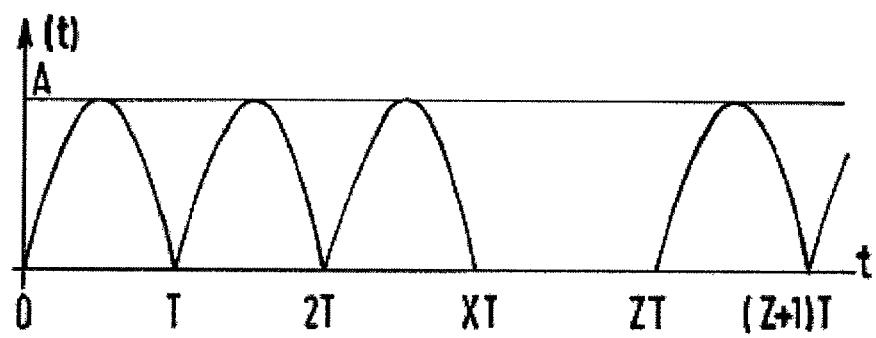
FIG. 4 shows the current signal passing through the heating element of the heating humidifier of FIG. 1 as a function of time.

The signal delivered to the heating element is shown in FIG. 4. It is a rectified sinusoidal signal with double alternation of amplitude A and period T, canceled between times XT and ZT. One can therefore write:

| | | |
|---|---|---|
| between 0 and XT: | $l(t) = A \sin(\omega)$ | with $\omega = 2\pi/2T = \pi/T$ |
| between XT and ZT: | $l(t) = 0$ | |

"Alternation" is used to denote the half-period of the sinusoidal signal, i.e., the period of the rectified sinusoidal signal.

X is therefore the number of passing half-cycles and Z the number of total half-cycles (passing and blocked).

The delivered electrical power to the heating element is:

$$P = Ueff \times Ieff = R \times Ieff^2 \quad \text{Equation 4}$$

Hence, $Ieff = \sqrt{\dfrac{1}{ZT} \times \int_0^{XT} f^2(t)dt}$ and $Im\,oy = \dfrac{1}{ZT} \times \int_0^{XT} f(t)dt$ Therefore:

$$Ieff^2 = \dfrac{1}{ZT} \times \int_0^{XT} A^2 \dfrac{1}{2}(1 - \cos(2wt))dt \quad Im\,oy = \dfrac{1}{ZT} \times \int_0^{XT} A \sin(wt)dt$$

$$Ieff^2 = \dfrac{A^2}{2T} \times \dfrac{X}{Z} \int_0^T \left(1 - \cos\left(\dfrac{2\pi}{T} \times t\right)\right)dt \quad Im\,oy = \dfrac{A}{T} \times \dfrac{X}{Z} \int_0^T \sin\left(\dfrac{\pi}{T} \times t\right)dt$$

$$Ieff^2 = \dfrac{A^2}{2} \times \dfrac{X}{Z} \quad Im\,oy = \dfrac{2A}{\pi} \times \dfrac{X}{Z}$$

Hence: $\dfrac{Im\,oy}{Ieff^2} = \dfrac{2A}{\pi} \times \dfrac{X}{Z} \times \dfrac{2Z}{A^2 X} = \dfrac{4A}{A^2 \pi} = \dfrac{4}{A\pi}$ And: $Ieff^2 = \dfrac{A\pi}{4} \times Im\,oy$ Equation 4 can therefore be written:

$$P = \frac{R \times Im\,oy \times Im\,ax \times \pi}{4} = \frac{U\max \times Im\,oy \times \pi}{4}$$

car $R \times I\max = U\max$, because $sR \times I\max = U\max$

The peak line voltage value (Umax) being constant, one can therefore write:

$$P = cte \times Iav$$

The principle regulation is therefore as follows: the reference power Pc may be regulated by the user of the heating element according to his preferences. The reference value of Iav ($Iav_c$) may then be determined by the system, knowing Umax. The values of Pc, $Iav_c$ and Umax may be digitized by a microcontroller.

The average real current traversing the heating element, Iav, may be measured with a simple measurement resistance mounted in series with the heating element. The microcontroller may then compare Iav to $Iav_c$ and determine if the number of half-cycles traversing the heating element must be increased or reduced such that the value of Iav is stable and equal to $Iav_c$. For example, if Iav is greater than $Iav_c$, the number of half-cycles traversing the heating element must be reduced.

Figure 5:
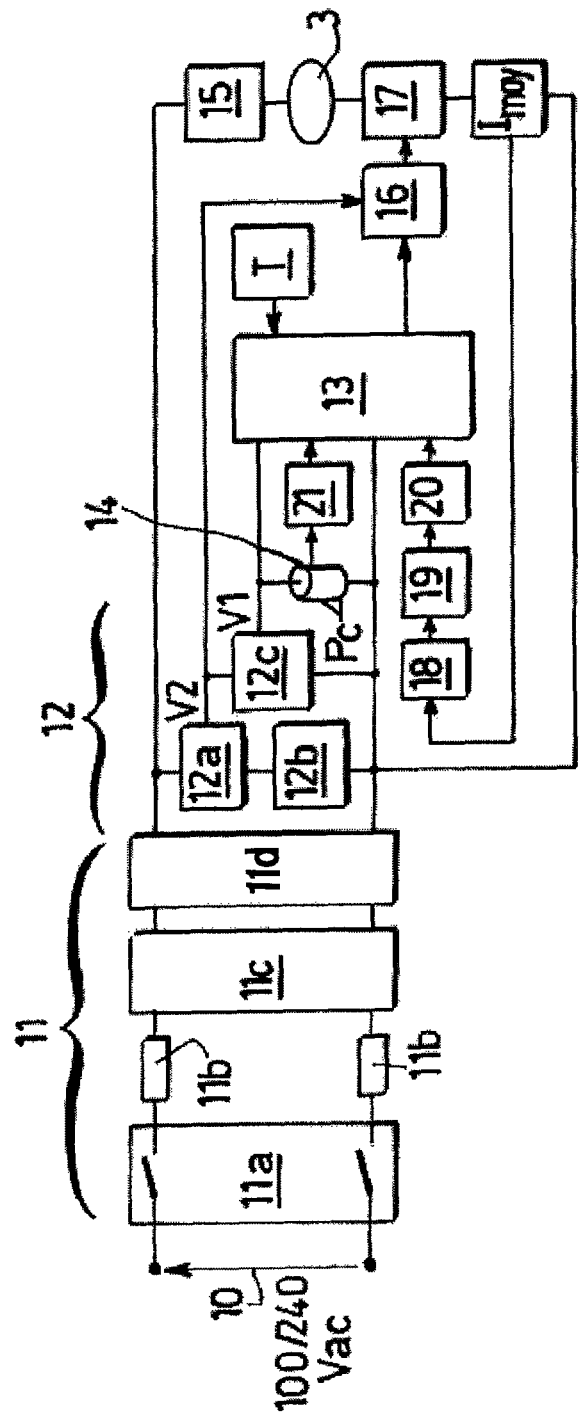
FIG. 5 is a diagram illustrating functioning of the heating humidifier of FIG. 1.

FIG. 5 is now referred to, which schematically illustrates the heating humidifier, as well as the means of supply and the associated controls.

The humidifier 1 may comprise an electronic card intended to be fed with line voltage 10, via an IEC C8 plug. A specific cord, furnished with the heating humidifier, may permit it to be connected to all available networks (varying according to country).

At the input of the electronic card, a filtering/protection device and device for rectification of the line voltage 10 may be provided.

A bipolar switch 11a may thus be provided, permitting cutoff of the electrical input on the electronic card, two fuses 11b of 2A that protect the electronic card, a filter 11c, represented by a capacitor, to avoid electromagnetic compatibility problems, and a varistor 11d, mounted in parallel at the line voltage input, to shunt any overvoltages carried by the line voltage.

The line voltage 10 may undergo double alternation rectification, so that the resistance of the heating element is supplied by a current, as shown in FIG. 4. The rectified voltage may also serve to create a power supply 12 of two DC voltages V1 and V2. A ballast transistor 12a, a voltage reference 12b and a regulator 12c may thus be provided.

Voltage V2 may be used for the control 16 of a control transistor 17 of the heating element, and to supply an operating amplifier (see below), whereas voltage V1 may supply a microcontroller 13.

Regulation of the power delivered to the heating element may be carried out by microcontroller 13, housed in the heating humidifier 1.

The microcontroller 13 may be present in a housing. It may include an ROM memory of the flash type, a RAM and EEPROM. It may include a 10-bit analog/digital converter, integrated with 4 multiplexed analog paths, an integrated analog comparator and an internal 4 MHz oscillator. It may also include a feed voltage drop detector and a watchdog.

The reference power Pc may be controlled by the potentiometer 14, accessible from the outside of the humidifier housing 1, so that the user 2 can choose the desired power, i.e., the desired level of humidification. The potentiometer 14 may be graduated from 1 to 5: position 5 (cursor at the maximum stop) delivers the maximum heating power and position 1 (cursor at the minimum stop) delivers a power equal to 20% of the maximum power, the other positions delivering a power proportional to the gradation. Use of the humidifier 1 without heating may require, if necessary, cutoff of the power supply to the humidifier with a switch.

The potentiometer 14 may be supplied by V1, which may guarantee that the analog input is never at a voltage greater than V1. Its value may be chosen to be comparable to the input impedance of microcontroller 13. The signal of potentiometer 14, freed of any parasitic signals by a filter capacitive 21, may be directly digitized by microcontroller 13.

The feed voltage (Umax) of the heating element may also be measured by microcontroller 13, which may digitize an analog voltage taken at the center point of a resistance bridge supplied by the voltage coming from the double-alternation rectification. The resistance bridge may be designed such that the voltage applied to the analog input of microcontroller 13 is always less than V1, whatever the line voltage 10 used to supply humidifier 1.

The current passing through the heating element (Iav) may be measured by measuring the voltage at the terminals of the small power resistor. The obtained signal on this resistor may first be filtered by a capacitor 18 to eliminate the parasitic signals, and may then be amplified by an operating amplifier 19, whose gain may be calculated, so that the signal remains less than V1, whatever the operating mode of the installation.

The amplifier output may then pass through a low-pass filter 20 (resistance/capacitance) with a low cutoff frequency to recover an analog signal that is an image of the average current value (Iav) passing through the heating element. This signal may finally be digitized by microcontroller 13.

Finally, the temperature T of the heated plate 3 may be measured by means of a thermistor of the CTN type, placed in the center of the lower face of plate 3. This thermistor may be included in a linearization bridge, including two resistors and fed by V1. The voltage from this bridge may then be digitized by microcontroller 13.

The heating element 3 may be controlled by a MOSFET transistor 17 of the N-channel type with enrichment. It may permit the current to pass through the heating resistor when a voltage VGS is applied to its gate. The importance of this component is to present an extremely low resistance to the passing state (RDSon), which may avoid a power loss at the level of the heating element and may limit the increase in temperature of the transistor.

In order to obtain the best possible resistance RDSon, the voltage VGS should not be less than 10 V. Hence, the digital control signal from the microcontroller may be limited.

The operating amplifier, fed by V2, may be used as a comparator, with a nominal commutation threshold of 2.96 V, to convert the signal of the microcontroller to a signal with a maximum value V2, which is applied to the gate of the MOSFET. The low output impedance of the amplifier may also permit a rapid commutation time of the transistor to be obtained.

The calibrated safety thermostat 15 may be mounted in series with the heating resistor. This thermostat 15, which may be in direct contact with the metal plate 3, may permit interruption of heating if the temperature T exceeds the safety vale. When the thermostat 15 is triggered, the electronic card may continue to function normally, but the resistance is no longer supplied. Only a mechanical action permits the thermostat to be reset.

Apart from the heating element, all the electronic components may be positioned directly on the printed circuit. The heating element may be connected on the electronic card by connectors that may permit simplification of assembly and reduce the assembly time. The card may be prescribed to be installed simply in the lower half-shell of the humidifier 1 and held by means of plastic clips.

The regulation program is now described, whose purpose may be to deliver a heating power P equal to a reference power Pc, controllable by user 2, whatever the line voltage 10 (85 to 264 Vac). Passage or blocking of the half-cycles may be carried out by an electronic control device capable of cutting off supply of the heating element, as previously indicated.

The values of Pc, Umax, Iav and temperature T of plate 3 may be digitized by microcontroller 13, via the analog/digital converter, and these values may then be used by the program.

Initially, the microcontroller 13 may allow a specified number of half-cycles out of 100 to pass through the heating element. The program may occur as follows.

In order to be synchronized relative to the wave cycles of the line voltage, the microcontroller 13 detects zero passage of the rectified wave. The line voltage is therefore not abruptly cut off.

The microcontroller 13 measures the value Umax of the line voltage, awaiting zero passage, and adds this value to the previously measured one. Once zero passage is detected, the microcontroller 13 decrements the counter of the number of passing half-cycles (X) and the counter of the total number of half-cycles (Z). If the number of passing half-cycles is equal to zero, then the microcontroller 13 blocks the half-cycles. Otherwise, the microcontroller 13 allows the half-cycles to pass.

The microcontroller 13 may then measure:
the current value passing through the heating element (Iav) and adds this value to the one previously measured; and
the temperature T of plate 3, and adds this value to the previously measured one.

The microcontroller 13 may then wait until the line voltage wave has reached its zero passage to restart the cycle.

When the total number of half-cycles equals zero, the microcontroller 13 may: calculate the average current passing through the heating element (Iav), calculate the line voltage value Umax, acquire the reference value (Pc), calculate the safety current value, compare the measured current value (Iav) to that of the reference ($Iav_c$) and the safety value, and calculate the average temperature value.

If $Iav<Iav_c$, an increase in Iav occurs and, for this purpose, the microcontroller will allow another alternation to pass through the heating element. Otherwise, if $Iav \geq Iav_c$, the microcontroller will allow one less alternation to pass through the heating element.

In the event that the safety current or a temperature T greater than, for example, 70° C., is surpassed, the microcontroller may block passage of the half-cycles. Moreover, if the current exceeds the maximum admissible current, the microcontroller may be placed in a waiting routine and will do nothing, except refresh the watchdog. If the temperature exceeds 70° C., the microcontroller may be placed in a routine, where it will continuously measure the temperature and refresh the watchdog. If the microcontroller measures the temperature less than 65° C., it may resume the principal loop.

To summarize, the processing phase may comprise:
decrementation of the counters (all half-cycles)
current measurement (all half-cycles)
measurement of the plate temperature (all half-cycles)
calculation of the average current (every 100 half-cycles)
calculation of the peak line voltage (every 100 half-cycles)
calculation of safety current (every 100 half-cycles)
calculation of the average current (every 100 half-cycles)
measurement of the reference Pc (every 100 half-cycles)
updating of the variables (every 100 half-cycles)
comparison of the average current with the reference current and the safety current (every 100 half-cycles)

Although the disclosed embodiments have been described in detail, it should be understood that various changes, substitutions and alterations can be made to the embodiments without departing from their spirit and scope.

What is claimed is:

1. A method for supplying a regulated degree of humidification (m) of air, the method comprising:
providing a water reservoir configured such that air contacting a surface of water in the reservoir is charged with humidity;
providing a heating device for heating the water in the reservoir by circulating an electric current;
measuring an average intensity (Iav) of the current passing through the heating device; and
controlling the average intensity (Iav) relative to a reference value (Iavc) to obtain a degree of humidification (m) of the air that is independent of an ambient temperature (Ta);
wherein the heating device is supplied with a rectified sinusoidal current including passing some half-cycles and blocking other half-cycles; and
wherein controlling the average intensity (Iav) comprises:
determining a count of the number of half-cycles passed to the heating device during a given time interval, and
controlling, based at least in part on the count of the number of passed half-cycles, the number of half-cycles passed to the heating device during the given time interval to regulate the average intensity (Iav) of the current passing through the heating device.

2. A method according to claim 1, further comprising:
storing a reference power (Pc) supplied to the heating device, the reference power (Pc) selected by a user;
measuring and storing a peak value (Umax) of a feed voltage for the heating device;
calculating the reference value (Iavc) of the average intensity of the current passing through the heating device based on the reference power (Pc) and the peak value (Umax) of the feed voltage, and storing the reference value (Iavc) of the average intensity;
measuring and storing the average intensity (Iav) of the current passing through the heating device;
comparing the measured value of the average intensity (Iav) and the reference value (Iavc) of the average intensity; and
controlling the number of passing half-cycles during a given time interval to reduce the difference between the measured value (Iav) of the average intensity and the reference value (Iavc) of the average intensity.

3. An apparatus for regulating the degree of humidification (m) of an air flow in contact with a surface of water located in a reservoir and intended to be delivered to a user, the apparatus comprising:
a heating device operable to heat the water by circulating an electric current;
means for measuring an average intensity (Iav) of the current passing through the heating device;
means for regulating the average intensity (Iav) relative to a reference value (Iavc), including:
a rectification device for rectification of the voltage delivered by the line voltage;

a counter for determining a count of the number of half-cycles passed to the heating device during a given time interval; and a blocking device operable to block some of the half-cycles of the voltage at 0;

wherein the rectification and blocking devices are configured such that the heating device can be supplied a rectified sinusoidal current including passing some half-cycles and blocking other half-cycles; and wherein the blocking device is operable to control, based at least in part on the count of the number of passed half-cycles, the number of half-cycles passed to the heating device during the given time interval as a function of the difference between the measured value (Iav) and the reference value (Iavc) of the average intensity.

4. An apparatus according to claim 3, further comprising:

selection means allowing a user to select a desired reference power (Pc);

means for measuring a peak value (Umax) of the feed voltage of the heating device and an average intensity (Iav) of the current passing through the heating device;

means for storing the reference power (Pc) and peak value (Umax) of the feed voltage;

means for calculating a reference value (Iavc) of the average intensity of the current passing through the heating device from the reference power (Pc) and the peak value (Umax) of the feed voltage;

means for storing the reference value (Iavc) of the average intensity and the measured average intensity (Iav);

means for comparing the measured value (Iav) and the reference value (Iavc) of the average intensity; and means controlled by the comparison device and operable to act on the power supply of the heating device to reduce the difference between the measured value (Iav) and the reference value (Iavc) of the average intensity.

5. A heating humidifier apparatus, comprising:

a water reservoir configured to house water;

a heating device operable to heat the water in the reservoir by circulating electric current;

an air input and output configured such that an air flow can circulate in contact with the surface of the water and be charged with humidity; and a control device for regulating the degree of humidification of the air flow, including:

means for measuring an average intensity (Iav) of the current passing through the heating device;

means for regulating the average intensity (Iav) relative to a reference value (Iavc);

a rectification device for rectification of the voltage delivered by the line voltage; and a blocking device operable to block some of the half-cycles of the voltage at 0;

wherein the rectification and blocking devices are configured such that the heating device can be supplied a rectified sinusoidal current including passing some half-cycles and blocking other half-cycles; and wherein the blocking device is operable to:

determine a count of the number of half-cycles passed to the heating device during a given time interval, and regulate the average intensity (Iav) relative to a reference value (Iavc) by controlling, based at least in part on the count of the number of passed half-cycles, the number of half-cycles passed to the heating device during the given time interval as a function of the difference between the measured value (Iav) and the reference value (Iavc) of the average intensity.

6. A heating humidifier apparatus according to claim 5, wherein the control device further comprises:

selection means allowing a user to select a desired reference power (Pc);

means for measuring a peak value (Umax) of the feed voltage of the heating device and an average intensity (Iav) of the current passing through the heating device;

means for storing the reference power (Pc) and peak value (Umax) of the feed voltage;

means for calculating a reference value (Iavc) of the average intensity of the current passing through the heating device from the reference power (Pc) and the peak value (Umax) of the feed voltage;

means for storing the reference value (Iavc) of the average intensity and the measured average intensity (Iav);

means for comparing the measured value (Iav) and the reference value (Iavc) of the average intensity; and means controlled by the comparison device and operable to act on the power supply of the heating device to reduce the difference between the measured value (Iav) and the reference value (Iavc) of the average intensity by controlling the number of passing half-cycles of a rectified sinusoidal current during a given time interval.

7. A method according to claim 1, wherein the voltage of the half-cycles supplied to the heating device is rectified line voltage.

8. An apparatus according to claim 3, wherein the voltage of the half-cycles supplied to the heating device is rectified line voltage.

9. A heating humidifier apparatus according to claim 5, wherein the voltage of the half-cycles supplied to the heating device is rectified line voltage.

* * * * *